(12) United States Patent
Jie et al.

(10) Patent No.: US 10,524,916 B2
(45) Date of Patent: Jan. 7, 2020

(54) RESORBABLE MACROPOROUS BIOACTIVE GLASS SCAFFOLD AND METHOD OF MANUFACTURE

(71) Applicant: NOVABONE PRODUCTS, LLC, Alachua, FL (US)

(72) Inventors: Qiang Jie, Xian (CN); Jiang Chang, Shanghai (CN); Weiming J. Gu, Shanghai (CN); Jipin Zhong, Gainesville, FL (US); Gregory J. Pomrink, Newberry, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 0 days.

(21) Appl. No.: 15/614,243

(22) Filed: Jun. 5, 2017

(65) Prior Publication Data

US 2017/0354501 A1    Dec. 14, 2017

Related U.S. Application Data

(60) Continuation-in-part of application No. 15/166,927, filed on May 27, 2016, now Pat. No. 9,707,079, and
(Continued)

(51) Int. Cl.
*C03C 14/00* (2006.01)
*A61F 2/28* (2006.01)
(Continued)

(52) U.S. Cl.
CPC ............... *A61F 2/28* (2013.01); *A61L 27/10* (2013.01); *A61L 27/56* (2013.01); *A61L 27/58* (2013.01); *C03B 19/06* (2013.01); *C03B 19/08* (2013.01); *C03C 3/062* (2013.01); *C03C 3/097* (2013.01); *C03C 3/112* (2013.01); *C03C 4/0007* (2013.01); *C03C 4/0014* (2013.01); *C03C 11/00* (2013.01);
(Continued)

(58) Field of Classification Search
CPC combination set(s) only.
See application file for complete search history.

(56) References Cited

U.S. PATENT DOCUMENTS 5,654,003 A    8/1997    Fuisz et al.
5,676,720 A    10/1997   Ducheyne et al.
(Continued)

FOREIGN PATENT DOCUMENTS

WO    WO 2007/0017756 A2    2/2007
WO    WO 201110053725 A1    5/2011
WO    WO 2015/0187207 A1    12/2015

OTHER PUBLICATIONS

Wu et al. Preparation of porous 45S5 Bioglass®-derived glass—ceramic scaffolds by using rice husk as a porogen additive. J Mater Sci: Mater Med (2009) 20: 1229.*
(Continued)

*Primary Examiner* — Noah S Wiese
(74) *Attorney, Agent, or Firm* — Brinks Gilson & Lione

(57) ABSTRACT

A method of manufacturing a resorbable, macroporous bioactive glass scaffold comprising approximately 15-45% CaO, 30-70% $SiO_2$, 0-25% $Na_2O$, 0-17% $P_2O_5$, 0-10% MgO and 0-5% $CaF_2$ by mass percent, produced by mixing with pore forming agents and specified heat treatments.

15 Claims, 12 Drawing Sheets

Specification includes a Sequence Listing.

Related U.S. Application Data a continuation-in-part of application No. 14/295,839, filed on Jun. 4, 2014, said application No. 15/166,927 is a continuation of application No. 12/798,660, filed on Apr. 6, 2010, which is a division of application No. 11/329,469, filed on Jan. 11, 2006, now Pat. No. 7,758,803.

(51) Int. Cl.

| | |
|---|---|
| C03B 19/08 | (2006.01) |
| C03C 4/00 | (2006.01) |
| C03C 3/112 | (2006.01) |
| C03C 3/097 | (2006.01) |
| C03C 3/062 | (2006.01) |
| A61L 27/58 | (2006.01) |
| A61L 27/56 | (2006.01) |
| A61L 27/10 | (2006.01) |
| C03C 11/00 | (2006.01) |
| C03B 19/06 | (2006.01) |
| C03C 12/00 | (2006.01) |
| A61F 2/30 | (2006.01) |
| A61F 2/46 | (2006.01) |

(52) U.S. Cl.
CPC .............. *C03C 12/00* (2013.01); *C03C 14/00* (2013.01); *C03C 14/008* (2013.01); *A61F 2/4644* (2013.01); *A61F 2002/2817* (2013.01); *A61F 2002/2835* (2013.01); *A61F 2002/30011* (2013.01); *A61F 2002/30032* (2013.01); *A61F 2002/30062* (2013.01); *A61F 2002/30224* (2013.01); *A61F 2002/30957* (2013.01); *A61F 2002/30968* (2013.01); *A61F 2210/0004* (2013.01); *A61F 2230/0069* (2013.01); *A61F 2250/003* (2013.01); *A61F 2250/0023* (2013.01); *A61F 2310/00329* (2013.01)

(56) References Cited

U.S. PATENT DOCUMENTS

| | | | |
|---|---|---|---|
| 5,811,302 A | 9/1998 | Ducheyne et al. | |
| 5,977,204 A | 11/1999 | Boyan et al. | |
| 6,054,400 A | 4/2000 | Brink et al. | |
| 6,083,522 A * | 7/2000 | Chu | A61B 17/0401 424/423 |
| 6,149,688 A | 11/2000 | Brosnahan et al. | |
| 6,344,496 B1 * | 2/2002 | Niederauer | A61F 2/28 523/113 |
| 6,607,557 B1 | 8/2003 | Brosnahan et al. | |
| 6,630,153 B2 | 10/2003 | Long et al. | |
| 6,767,854 B2 | 7/2004 | Berger et al. | |
| 7,241,486 B2 | 7/2007 | Pirhonen | |
| 7,758,803 B2 | 7/2010 | Chang et al. | |
| 8,029,575 B2 | 10/2011 | Borden | |
| 8,168,208 B1 | 5/2012 | El-Ghannam | |
| 8,177,854 B2 | 5/2012 | Borden | |
| 8,303,967 B2 * | 11/2012 | Clineff | A61L 27/10 424/400 |
| 8,337,876 B2 | 12/2012 | Liu et al. | |
| 9,199,006 B2 * | 12/2015 | Pomrink | A61L 27/24 |
| 9,199,032 B2 * | 12/2015 | McBride | A61L 27/46 |
| 2003/0180376 A1 | 9/2003 | Dalal et al. | |
| 2003/0219466 A1 | 11/2003 | Kumta et al. | |
| 2004/0002770 A1 | 1/2004 | King et al. | |
| 2004/0009598 A1 * | 1/2004 | Hench | C12N 5/0654 435/375 |
| 2004/0043053 A1 * | 3/2004 | Yu | A61L 27/10 424/426 |
| 2004/0167006 A1 | 8/2004 | Apel et al. | |
| 2004/0228905 A1 | 11/2004 | Greenspan et al. | |
| 2006/0093645 A1 | 5/2006 | Janas et al. | |
| 2006/0292198 A1 | 12/2006 | Dalal et al. | |
| 2007/0162151 A1 | 7/2007 | Chang et al. | |
| 2007/0224286 A1 | 9/2007 | Kutty et al. | |
| 2007/0275021 A1 | 11/2007 | Lee et al. | |
| 2008/0038534 A1 | 2/2008 | Zenati et al. | |
| 2008/0060382 A1 | 3/2008 | Rake et al. | |
| 2008/0066495 A1 | 3/2008 | Moimas et al. | |
| 2008/0187571 A1 | 8/2008 | Clineff et al. | |
| 2010/0179667 A1 | 7/2010 | Day et al. | |
| 2011/0081396 A1 * | 4/2011 | Denry | A61L 27/10 424/423 |
| 2011/0087291 A1 | 4/2011 | Justis et al. | |

OTHER PUBLICATIONS

Vissers et al., "Pore size regulates mesenchymal stem cell response to Bioglass-loaded composite scaffolds," *J Mater Chem B*, 3:8650-8658 (2015).

Yuan, et al., "Bone Induction by Porous Glass Ceramic Made from Bioglass® (45S5)," *J Biomed Mater Res (Appl Biomater)*, 58:270-276 (2001).

Notification Concerning Transmittal and International Preliminary Report on Patentability received in PCT Application No. PCT/US2015/012046 dated Dec. 15, 2016.

Hench, et al., "Bonding Mechanisms at the Interface of Ceramic Prosthetic Materials," *J. Biomed. Mater. Res. Symposium*, 2(1):117-141 (1971).

Xynos, et al., "Ionic Products of Bioactive Glass Dissolution Increase Proliferation of Human Osteoblasts and Induce Insulin-like Growth Factor II Mrna Expression and Protein Synthesis," *Biochemical and Biophysical Research Communications*, 276:461-465 (2000).

Xynos, et al., "Gene-expression profiling of human osteoblasts following treatment with the ionic products of Bioglass® 45S5 dissolution," *J. Biomed. Mater. Res.*, 55:151-157 (2001).

Xynos, et al., "Bioglass® 45S5 Stimulates Osteoblast Turnover and Enhances Bone Formation In Vitro: Implications and Applications for Bone Tissue Engineering,"*Calcif. Tissue Int.*, 67:321-329 (2000).

International Search Report and Written Opinion received in PCT Application No. PCT/US2015/012046 dated May 5, 2015.

Supplementary European Search Report received in EP Application No. EP 15803957.8 dated Dec. 13, 2017.

\* cited by examiner

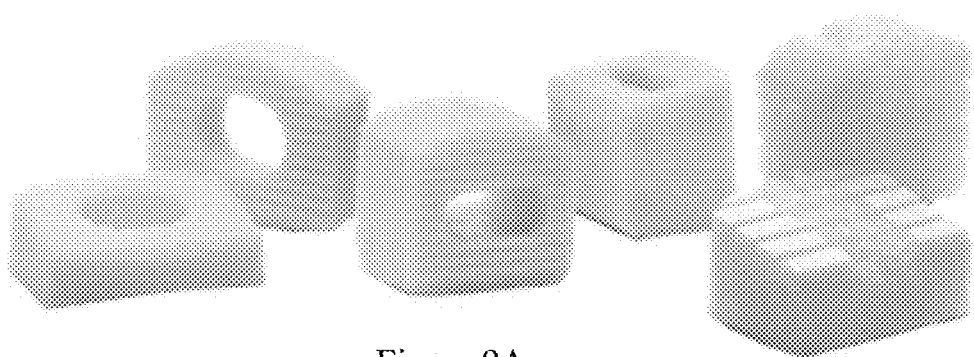
Figure 9A
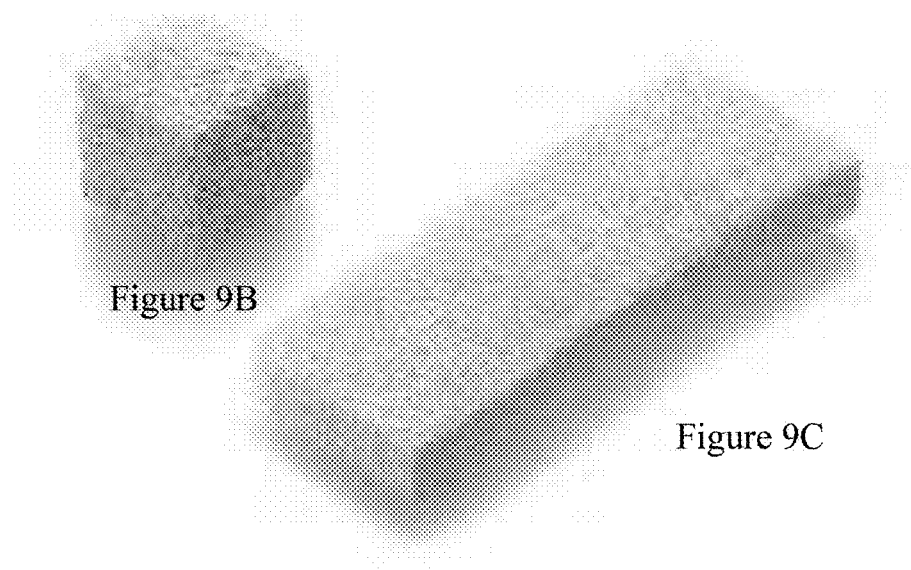
Figure 9B
Figure 9C

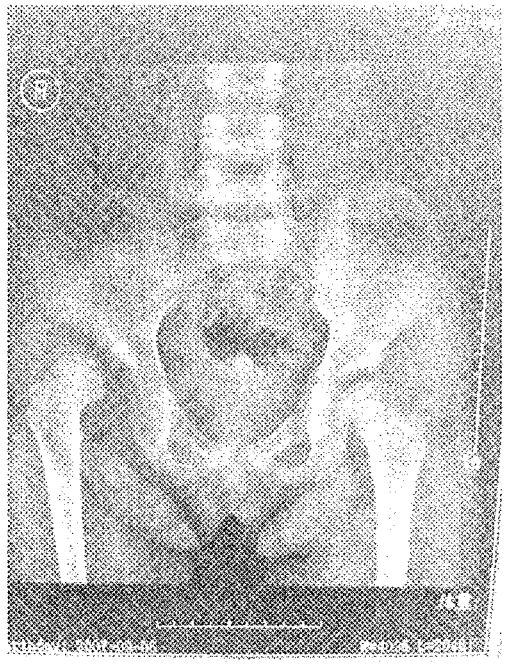
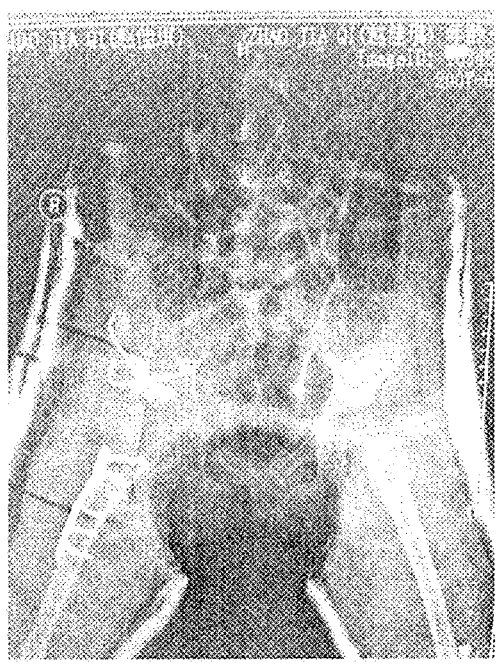
Figure 11A     Figure 11B
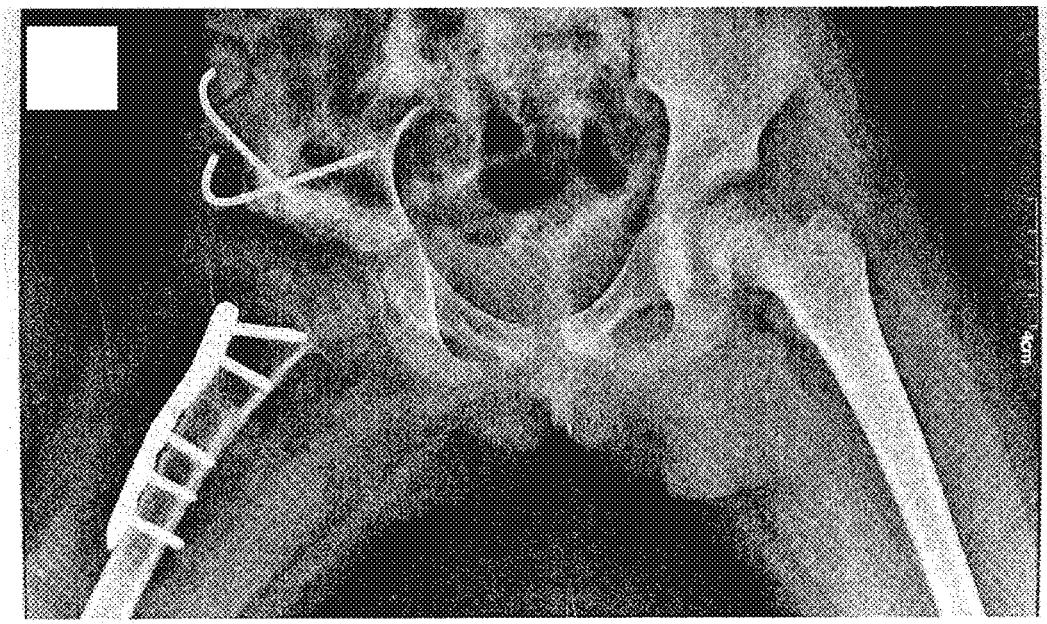
Figure 11C

SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: artificial peptide, bone resorption inhibitor,
      WP9QY(W9)

<400> SEQUENCE: 1

Tyr Cys Trp Ser Gln Tyr Leu Cys Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: artificial bone targeting peptide

<400> SEQUENCE: 2

Asp Asp Asp Asp Asp Asp
1               5

<210> SEQ ID NO 3
<211> LENGTH: 8
<212> TYPE: PRT
<213> ORGANISM: Artificial Sequence
<220> FEATURE:
<223> OTHER INFORMATION: artificial bone targeting peptide

<400> SEQUENCE: 3

Asp Asp Asp Asp Asp Asp Asp Asp
1               5

<210> SEQ ID NO 4
<211> LENGTH: 18
<212> TYPE: PRT
<213> ORGANISM: Artificial Sequence
<220> FEATURE:
<223> OTHER INFORMATION: artificial bone targeting peptide

<400> SEQUENCE: 4

Asp Ser Ser Asp Ser Ser Asp Ser Ser Asp Ser Ser Asp Ser Ser Asp
1               5                   10                  15

Ser Ser

RESORBABLE MACROPOROUS BIOACTIVE GLASS SCAFFOLD AND METHOD OF MANUFACTURE

RELATED APPLICATIONS

The present patent application is a continuation-in-part application of U.S. patent application Ser. No. 15/166,927, filed May 27, 2016, which is a continuation application of U.S. patent application Ser. No. 12/798,660, filed Apr. 6, 2010, which is a divisional application of and claims the benefit of U.S. patent application Ser. No. 11/329,469, filed Jan. 11, 2006 now issued U.S. Pat. No. 7,758,803, contents of which are incorporated herein in their entirety.

Also, the present patent application is a continuation-in-part application of U.S. patent application Ser. No. 14/295,839, filed Jun. 4, 2014, contents of which are incorporated herein in its entirety.

SEQUENCE LISTING

The instant application contains a Sequence Listing, which has been submitted electronically in ASCII format and is hereby incorporated by reference in its entirety.

BACKGROUND

Biomaterials involving resorbable or degradable, macroporous bioactive glass material, which can be used either for the restoration of hard tissues or as the tissue engineering scaffold, as well as preparation methods for such materials is described herein. Also, bone graft compositions that include a bioactive glass scaffold and are characterized in that the bioactive glass scaffold has a high compressive strength, is osteoconductive and osteostimulative and resorbs at a rate consistent with the formation of new bone, are described. Also, methods of using the bone graft compositions for regeneration of hard tissues, especially for joint reconstruction (such as in, e.g., developmental dysplasia (dislocation) of the hip or DDH, and tibial plateau elevation), cranial reconstruction and spine fusion, are provided.

Autogenous bone grafts are often the gold standard for regeneration of hard tissues in adults as well as children. The drawbacks, however, are the harvest time, donor site morbidity, graft resorption, modeling changes, and harvest volume limitations. The clinician has to choose the site of bone harvest wisely, taking into account the nature of the reconstruction and volume requirements.

Also, due to the limited quantity of autogenous bone, especially in children, an additional bone graft is needed to satisfactorily reconstruct hard tissue. Allografts have been used for this purpose. However, the use of allografts may result in problems, such as an increased risk of disease transmission along with possible graft rejection that could result in delayed healing and biomechanical failure of the reconstructed bone.

Also, currently available synthetic bone grafts and bone cements are incapable of providing the mechanical strength necessary while being resorbed by the body and replaced with new bone. More specifically, putties and particulate graft materials have often insufficient strength and do not maintain their position in the surgical site. Methacrylates are not resorbable and replaced with new bone while calcium phosphates and calcium phosphate cements have an insufficient resorption profile or are too weak for use in certain hard tissue repairs, such as in hip reconstruction.

Clinically, the ideal graft material for hard tissue reconstruction should be (1) highly bioactive, (2) should stimulate the activity of bone forming cells, (3) should possess sufficient mechanical strength to support the filled space, (4) function as an osteoconductive scaffold to promote new bone growth to accelerate healing of the defect, and (5) should be resorbed at a rate consistent with the formation of new bone to assure the success of the reconstruction.

"Bioactive glass" or "bioglass," for example, 45S5, contains 45% silica, 24.5% calcium oxide, 24.5% sodium oxide and 6% phosphate by weight is highly bioactive possessing the fastest biological response when implanted in living tissue among all of the bioactive glass compositions. Since the first report by Hench et al. (L. L. Hench, R. J. Splinter, T. K. Greelee, and W. C. Allen, "Bonding Mechanisms at the Interface of Ceramic Prosthetic Materials", J. Biomed. Mater. Res., No. 2, 117-141, 1971) that Bioglass compositions could bond with bone chemically, bioactive glass has been considered a material that demonstrates a fast biological response (greater bioactivity) than any other material.

Also, such glass material has been used for restoration of bone defects in clinical practice for over ten years, and such clinical applications have proven successful in that this glass can bring along not only the benefit of osteoconduction, but also the bioactivity to stimulate the growth of bone tissues. Many recent studies have revealed that the degradation products of bioactive glass can enhance the generation of growth factors, facilitate cellular proliferation and activate gene expression of osteoblasts. Moreover, bioactive glass is the only synthetic biomaterial so far that can both bond with bone tissues and soft tissues. These unique features of this glass have created a great potential for its clinical application as a type of medical device, and thereby, attracted great attention from both academia and the industrial sector. Despite its excellent biocompatibility and bioactivity, bioactive glass can be now produced only in a granular form for clinical application. For restoration of bone defects, macroporous and block scaffold materials with a particular mechanical strength are often needed to fill in and restore such defects. Even in the field of tissue engineering, which receives worldwide attention and evolves rapidly, macroporous bioactive scaffold materials are similarly demanded to serve as cell carriers.

As a result, bioglass products have been cleared by the U.S. Food and Drug Administration (FDA) as osteostimulative. The stimulation of osteoblast proliferation and differentiation has been evidenced during in vitro osteoblast cell culture studies by increased DNA content and elevated osteocalcin and alkaline phosphatase levels. Bioglass with osteostimulative properties can enhance the production of growth factors, promote the proliferation and differentiation of bone cells (I. D. Xynos, A. J. Edgar, and L. D. K. Buttery et al, "Ionic Products of Bioactive Glass Dissolution Increase Proliferation of Human Osteoblasts and Induce Insulin-like Growth Factor II mRNA Expression and Protein Synthesis," Biochem. and Biophysi. Res. Comm. 276, 461-65, 2000; I. D. Xynos, A. J. Edgar, and L. D. K. Buttery et al, "Gene-Expression Profiling of Human Osteoblasts Following Treatment with the Ionic Products of Bioglass® 45S5 Dissolution," J. Biomed. Mater. Res., 55, 151-57, 2000; and I. D. Xynos, M. V. J. Hukkanen, J. J. Batten et al, "Bioglass® 45S5 Stimulates Osteoblast Turnover and Enhance Bone Formation In Vitro: Implications and Applications for Bone Tissue Engineering," Calcif. Tissue Int., 67, 321-29, 2000), and stimulate new bone formation with new bone observed simultaneously at the edge and center of the defect area.

U.S. Pat. No. 7,705,803 to Chang et al. discusses a resorbable, macroporous bioactive glass scaffold produced by mixing with pore forming agents and specified heat treatments. The '803 patent also describes the method of manufacture for the porous blocks. The compressive strength of the bioglass scaffold described by Chang et al. is 1-16 MPa.

As such, bioglass-based graft materials for hard tissue reconstructions, including in DDH and other related bone conditions, having a relatively high compressive strength especially for use in application that require high load bearing implant materials may be desirable. Also, the known procedures could benefit from advancements in techniques, instrumentation, and materials to make the results more reproducible and reliable.

Research studies in the past have suggested that besides the composition of the material, its structure can directly influence its clinical applications as well. The macroporous and block scaffold materials with bioactivity whose pore sizes are in the range of 50-500 microns are most suitable to be used as materials either for the restoration of bone defects, or as cell scaffolds. Any macroporous biomaterial having a pore size within the said range can bring benefits to the housing and migration of cells or tissue in-growth, as well as to the bonding of such a material to living tissues, thereby achieving the goals of repairing defects in human tissues and reconstructing such tissues more effectively.

Moreover, the subject of the biomaterials that are both resorbable and macroporous has now become an integral part of tissue engineering studies that have been rapidly developed in recent years, where scaffolds made of such macroporous materials can be adopted to serve as cell carriers so that cells can grow in the matrix materials and constitute the living tissues that contain genetic information of the cell bodies, and such tissues can be in turn, implanted into human bodies to restore tissues and organs with defects. Therefore, resorbable, macroporous bioactive glass scaffold materials possess wide-ranging potential for their applications as cell scaffolds either for restoration of defects in hard tissues, or for the purpose of in vitro culture of bone tissues.

U.S. Pat. Nos. 5,676,720 and 5,811,302 to Ducheyne, et al, teach a hot-pressing approach using inorganic salts such as calcium carbonate and sodium bicarbonate as the pore-forming agents to prepare and manufacture macroporous bioactive glass scaffolds which have the compositions of $CaO$—$SiO_2$—$Na_2O$—$P_2O_5$, and which are designed to function as the cell scaffolds used for in vitro culture of bone tissues. Nevertheless, this hot-pressing approach if adopted would entail high production costs, and furthermore, controlling the composition of the finished products is difficult because the composition will be affected by the remnants that result after sintering the inorganic salts used as pore-forming agents. Additionally, Yuan, et al. have adopted oxydol as a foaming agent to prepare and manufacture 45S5 bioactive glass scaffolds under a temperature of 1000° C., with the scaffolds produced in this way being bioactivity and having the ability to bond together with bone tissues Q. Biomed. Mater. Res; 58:270-267, 2001). But according to our testing results, the glasses will become substantially crystallized and their resorbability/degradability will decrease if they are sintered under a temperature of 1000° C. In addition, it is quite difficult to control the pore size and pore number of the materials when oxydol is used as the foaming agent.

Mechanical strength is also an important factor for performance of macroporous bioactive glass scaffold materials, and relevant studies have suggested that any compressive strength below 1 MPa would result in the poor applicability of these scaffold materials, and thus, in the course of applying them either as cell scaffolds or for the purpose of restoration of bone injuries, such materials would be very prone to breakage or damage, therefore limiting the effectiveness of their application. So far, no report on the compressive strength standard data of macroporous bioactive glass scaffolds has been found in previous patent and published documents and as a result, gives rise to the purpose of this invention to determine proper technical control measures to keep the compressive strength of the manufactured bioactive glass scaffold within a certain range to meet the requirements of various applications.

SUMMARY

The purpose of this invention is to develop, through the optimization of technology and process, a new type of macroporous bioactive glass scaffold with interconnected pores, which features excellent bioactivity, biodegradability, controllable pore size and porosity. Such a scaffold would serve as a means to repair defects in hard tissues and be applied in the in vitro culture of bone tissues, and its strength can be maintained within a range of 1-16 MPa in order to meet demands arising from the development of the new-generation biological materials and their clinical applications.

This invention has been designed to use glass powders as raw material, into which organic pore forming agents will be added, and the mixture will be processed by either the dry pressing molding method or gelation-casting method, and then the resulting products will be obtained by sintering under appropriate temperatures. In this way, a macroporous bioactive glass scaffold can be obtained with various porosities, pore sizes and pore structures, as well as different degrees of compressive strength and degradability. The chemical composition of such scaffolds shall be expressed as CaO 24-45%, $SiO_2$ 34-50%, $Na_2O$ 0-25%, $P_2O_5$ 5-17%, MgO 0-5 and $CaF_2$ 0-1%. Additionally, the approaches provided in this invention can be adopted to prepare the said scaffold in different shapes. The crystallizations of calcium phosphate and/or calcium silicate can be formed inside the bioactive glass scaffolds by way of technical control, whereby both the degradability and mechanical strength of the macroporous materials can be controlled as demanded.

As designed in this invention, the macroporous bioactive glass scaffold materials exhibit excellent biological activity, and can release soluble silicon ions with precipitation of bone-like hydroxyl-apatite crystallites on their surface in just a few hours after being immersed into simulated body fluids (SBF). In addition, the macroporous bioactive glass in this invention is resorbable, as shown by in vitro solubility experiments, and such glass demonstrates a degradation rate of approximately 2-30% after being immersed in simulated body fluids (SBF) for 5 days. As such, it can be concluded that the macroporous bioactive glass scaffold materials in this invention do not only have desirable biointerfaces and chemical characteristics, but also demonstrate excellent resorbability/degradability.

Another feature of this invention is manifested in controlling technical conditions to create materials that can have both a relatively higher porosity (40-80%) with suitable pore size (50-600 microns), and exhibit a proper mechanical strength (with the compressive strength at 1-16 MPa).

Certain embodiments relate to a resorbable, macroporous bioactive glass scaffold comprising in mass percents approximately 15-45% CaO, 30-70% $SiO_2$, 0-25% $Na_2O$, 0-17% $P_2O_5$, 0-10% MgO and 0-5% $CaF_2$, wherein the bioactive glass scaffold has a porosity of between approximately 40-80 volume percent, pore size ranging from approximately 50-600 microns, and interconnected pores. The bioactive glass scaffold can comprise approximately 24.5% CaO, 45% $SiO_2$, 24.5% $Na_2O$ and 6% $P_2O_5$ and have a porosity of approximately 56 volume percent; alternatively, the bioactive glass scaffold can comprise approximately 40.5% CaO, 39.2% $SiO_2$, 4.5% MgO, 15.5% $P_2O_5$ and 0.3% $CaF_2$ and have a porosity of approximately 55 volume percent. The bioactive glass scaffold may further comprise at least one of precipitated calcium phosphate or calcium silicate crystals. The bioactive glass scaffold may have a compressive strength of between approximately 1 to 100 MPa; alternatively, 1 to 16 MPa. The bioactive glass scaffold can comprise a side surface, wherein at least a portion of the side surface comprises a plurality of protrusions to facilitate prevention of expulsion or dislocation of the bioactive glass scaffold once installed in a patient. The bioactive glass scaffold may be in a predetermined configuration selected from the group consisting of a block, a wedge, a dowel, a strip, a sheet, a strut, a disc. The bioactive glass scaffold may further comprise a glycosaminoglycan selected from the group consisting of heparin, heparan sulfate, chondroitin sulfate, dermatan sulfate, keratan sulfate, and hyaluronic acid. The bioactive glass scaffold may further comprise one or more of surface-immobilized peptides, growth factors and therapeutic agents. The peptides may be selected from the group consisting of WP9QY (W9; SEQ ID NO: 1), OP3-4, RANKL, B2A, P1, P2, P3, P4, P24, P15, TP508, OGP, PTH, NBD, CCGRP, $(Asp)_6$ (SEQ ID NO:2), $(Asp)_8$ (SEQ ID NO:3), $(Asp, Ser, Ser)_6$ (SEQ ID NO:4), and mixtures thereof. The bioactive glass scaffold may be pre-treated with blood, PRP, bone marrow or a bone marrow concentrate to provide signaling proteins and cells to further enhance the regeneration of the hard tissues.

In certain embodiments, the bioactive glass scaffold described herein may be used as material for the restoration of injured hard tissues in a subject.

In other certain embodiments, the bioactive glass scaffold described herein may be used as the cells support scaffold for in vitro culture of bone tissue.

In further embodiments, the bioactive glass scaffold described herein may be used as a replacement or support for living bone materials in surgical procedures requiring the use of bioactive glass scaffold.

In yet other embodiments, the bioactive glass scaffold described herein may be used in a joint reconstruction procedure, tibial plateau elevation procedure, craniomaxillofacial reconstruction, spine fusion procedure, or treating or correcting developmental dysplasia of the hip in a subject.

Certain further embodiments relate to a method of treating or correcting developmental dysplasia of the hip in a subject comprising resecting the bone to create a resection, and placing the bioactive glass scaffold described herein in the resection such that the bioactive glass scaffold spans the resection.

BRIEF DESCRIPTION OF THE DRAWINGS

FIGS. 9A, 9B, and 9C depict exemplary shapes of the bone grafts; (A) dowel, (B) block, and (C) sheet.

FIG. 11A depicts an x-ray of an undeveloped cup of a patient before insertion of a bone graft.

FIG. 11B depicts an x-ray showing a bioglass block used (arrow) for the hip cup re-constructions following the surgery.

FIG. 11C depicts an x-ray showing a bioglass block used (arrow) for the hip cup re-constructions 8 weeks after the surgery.

DETAILED DESCRIPTION OF THE DRAWINGS AND THE PRESENTLY PREFERRED EMBODIMENTS

Figure 1:
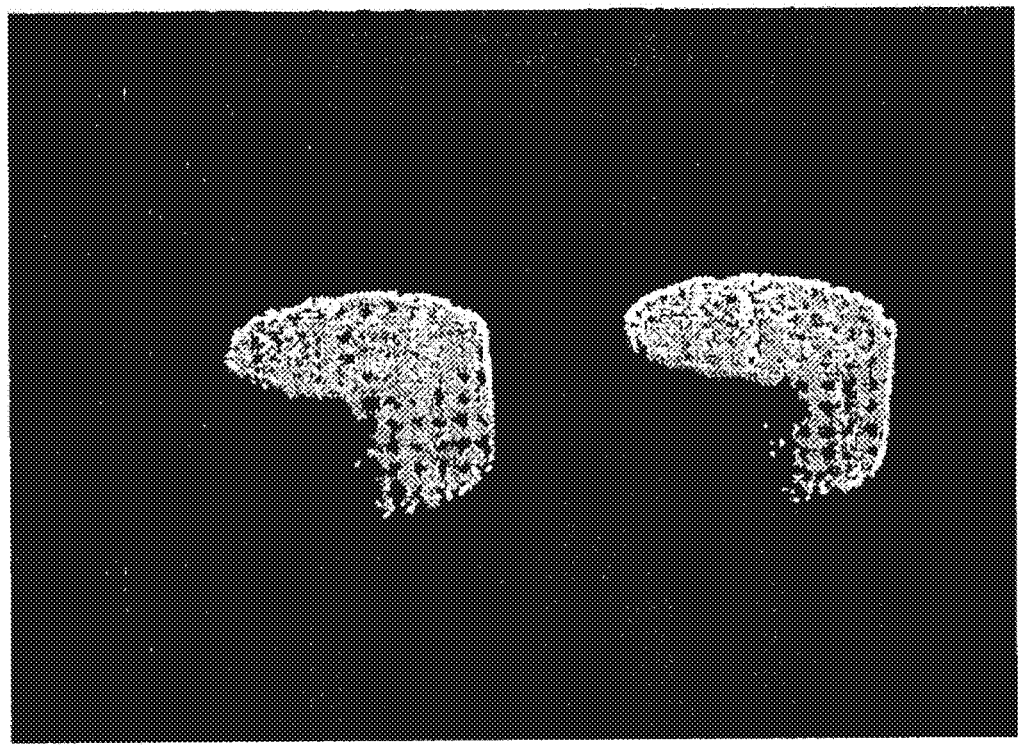
FIG. 1 is a photograph of the prepared macroporous bioactive glass.

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

The following relates to a new type of macroporous bioactive glass scaffold with interconnected pores, which features high strength (1-100 MPa), excellent bioactivity, biodegradability, controllable pore size and porosity. The bioactive glass scaffold is osteoconductive, osteostimulative, and resorbs at a rate consistent with the formation of new bone. Such a scaffold would serve as a means to repair defects in hard tissues, such as joints (e.g., in developmental dysplasia (dislocation) of the hip or DDH, and tibial plateau elevation), cranial reconstruction and spine fusion and can be applied in the in vitro culture of bone tissues.

One advantage of the bone grafts described herein is that the bone grafts include a strong, bioactive, bioresorbable and load bearing bioglass scaffold that facilitates the regeneration of hard tissues.

This bone graft/implant material is prepared using high temperature treatment of Bioglass to form a high strength material in various shapes which can be used clinically as an implant for the patients with an undeveloped hip (developmental hip dysplasia or DDH) requiring reconstruction. This high strength Bioglass block can be also used for other bone defects repair where load bearing is needed, including osteotomy wedges to elevate the tibial plateau, treatment of compression fractures and other bone anomalies requiring the insertion of a bone graft to alter the angle of an articulating joint or change the axis or length of a bone, which was compromised through a congenital defect or trauma. In addition, this material can function as an intervertebral spacer to promote spine fusion. Other applications of high strength bioresorbable, osteostimulative, osteoconductive bone graft/implants can be found in craniomaxillofacial reconstruction along with surgical procedures which require these properties.

The macroporous bioactive glass scaffold materials described herein exhibit excellent biological activity, and can release soluble silicon ions with precipitation of bone-like hydroxyl-apatite crystallites on their surface in just a few hours after being immersed into simulated body fluids (SBF). In addition, the macroporous bioactive glass is resorbable, as demonstrated by in vitro solubility experiments, and such glass demonstrates a degradation rate of approximately 2-30% after being immersed in simulated body fluids (SBF) for 5 days. As such, the macroporous bioactive glass scaffold materials do not only have desirable biointerfaces and chemical characteristics, but also demonstrate excellent resorbability/degradability.

1. Bone Graft 1.1. Composition

Certain embodiments relate to bone graft compositions. Specifically, certain embodiments relate to bone graft compositions that include a body formed to define a predetermined configuration.

The body of the bone graft includes a resorbable, macroporous bioactive glass scaffold.

Bioactive glass scaffold suitable for the present compositions and methods may be prepared from bioactive glass and/or ceramics and includes calcium sodium phosphosilicate particles or calcium phosphate particles, or combinations thereof. In some embodiments, sodium phosphosilicate particles and calcium phosphate particles may be present in the compositions in an amount of about 1% to about 99%, based on the weight of sodium phosphosilicate particles and calcium phosphate particles. In further embodiments, calcium phosphate may be present in the composition in about 1%, about 2%, about 3%, about 4%, about 5%, about 6%, about 7%, about 8%, about 9%, or about 10%. In certain embodiments, calcium phosphate mat be present in the composition in about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90 to about 95%, or about 95 to about 99%. Some embodiments may contain substantially one of sodium phosphosilicate particles and calcium phosphate particles and only traces of the other. The term "about" as it relates to the amount of calcium phosphate present in the composition means±0.5%. Thus, about 5% means 5±0.5%.

The bioactive glass scaffold may further comprise one or more of a silicate, borosilicate, borate, strontium, or calcium, including SrO, CaO, $P_2O_5$, $SiO_2$, and $B_2O_3$. An exemplary bioactive glass is 45S5, which includes 46.1 mol % $SiO_2$, 26.9 mol % CaO, 24.4 mol % $Na_2O$ and 2.5 mol % $P_2O_5$. An exemplary borate bioactive glass is 45S5B1, in which the $SiO_2$ of 45S5 bioactive glass is replaced by $B_2O_3$. Other exemplary bioactive glasses include 58S, which includes 60 mol % $SiO_2$, 36 mol % CaO and 4 mol % $P_2O_5$, and S70C30, which includes 70 mol % $SiO_2$ and 30 mol % CaO. In any of these or other bioactive glass materials, SrO may be substituted for CaO.

The following composition, having a weight % of each element in oxide form in the range indicated, will provide one of several bioactive glass compositions that may be used to form a bioactive glass ceramic:

| | |
|---|---|
| $SiO_2$ | 0-86 |
| CaO | 4-35 |
| $Na_2O$ | 0-35 |
| $P_2O_5$ | 2-15 |
| $CaF_2$ | 0-25 |
| $B_2O_3$ | 0-75 |
| $K_2O$ | 0-8 |
| MgO | 0-5 |
| CaF | 0-35 |

In certain embodiments, bioactive glass scaffold include glasses having about 15-45% CaO, 30-70% $SiO_2$, 0-25% $Na_2O$, 0-17% $P_2O_5$, 0-10% MgO and 0-5% $CaF_2$. The crystallizations of calcium phosphate and/or calcium silicate can be formed inside the bioactive glass scaffolds by way of technical control, whereby both the degradability and mechanical strength of the macroporous materials can be controlled as demanded.

The bioactive glass scaffold can be in the form of a three-dimensional compressible body of loose glass-based particles or fibers in which the particles or fibers comprise one or more glass-formers selected from the group consisting of $P_2O_5$, $SiO_2$, and $B_2O_3$. Some of the fibers have a diameter between about 100 nm and about 10,000 nm, and a length:width aspect ratio of at least about 10. The pH of the bioactive glass can be adjusted as-needed.

The bioactive glass material may be ground with mortar and pestle prior to converting it to a paste. Any other method suitable for grounding the bioactive glass material may be used. In one embodiment, the ground bioactive glass material may be mixed with other constituents to produce templates or granules that may be formed into a paste that can be shaped before further treatments are made. For example, a suitable bioresorbable polymer may be used to prepare a paste of a bioactive material (for example, glass or ceramic material). In one embodiment, a paste of a non-crystalline, porous bioactive glass or ceramic material is prepared that permit in vitro formation of bone tissue when exposed to a tissue culture medium and inoculated with cells.

Exemplary bioresorbable polymers include polyethylene glycol (PEG), PVA, PVP, PAA, PLA, PGA, PLGA, polysebacate, polyalkylene oxides, polyaspartates, poly-succinimides, polyglutamates, poldepsipeptides, resorbable polycarbonates, etc.

A macroporous bioactive glass scaffold can be obtained with various porosities, pore sizes and pore structures, as well as different degrees of compressive strength, resorption and degradability.

The implants can be prepared with a range of desired mechanical and chemical properties combined with pore morphology to promote osteoconductivity.

In certain embodiments, the bone graft is characterized in that the bioactive glass scaffold has a compressive strength strong enough to support the reconstruction defect space but at the same time has high porosity (up to about 90%) to slow the integration of the host tissue and subsequently reduce the resorption time. More specifically, the compressive strength of the implant can range from approximately 1 MPa to approximately 100 MPa. Alternatively, the compressive strength can be in the range of approximately 25-75 MPa; alternatively, approximately, 10-100 MPa; alternatively, approximately 5-10 MPa; alternatively, approximately 18-40 MPa. In certain embodiments, the bone graft is characterized in that the bioactive glass scaffold has a compressive strength of at least approximately 10 MPa, at least approximately 15 MPa, at least approximately 20 MPa, at least approximately 25 MPa, at least approximately 30 MPa, at least approximately 40 MPa, or at least approximately 50 MPa.

For example, the compressive strength of the bone graft can range from approximately 5 MPa to 10 MPa for treatment of DDH and osteotomy wedges for tibial plateau reconstruction while intervertebral spacers require a higher strength implant ranging from approximately 25 to approximately 75 MPa for spine fusion. In certain instances, treatment of DDH and osteotomy wedges for tibial plateau may require bone grafts having a higher strength, e.g., at least approximately 10 MPa.

The porosity of the bone graft may also vary. In certain embodiments, construction porosities as high as 90% may be achieved under suitable conditions. For example, the bone graft may have porosity of approximately 10-90 volume percent; alternatively, approximately 20-80 volume percent; alternatively, approximately 25-75 volume percent; alternatively, approximately 40-60 volume percent. Other porosity ranges may also be suitable.

The pores in the bioactive glass material range from about 5 microns to about 5100 microns with an average pore size of $100\pm50$ microns, $200\pm50$ microns, $300\pm50$ microns, $400\pm50$ microns, $500\pm50$ microns, $600\pm50$ microns, $700\pm50$ microns, $800\pm50$ microns or $900\pm50$ microns.

Another important factor for the clinical success of the bioglass grafts is that the bioglass scaffold should be optimized to maintain a significant percentage (>30%) of its initial mechanical properties for the first 1-3 months after implantation. Otherwise, a rapid decrease in mechanical strength of an implant within the surgical site may lead to implant failure while insufficient resorption may result in delayed healing.

In certain further embodiments, the particles of bioactive glass may be coated with a glycosaminoglycan, wherein the glycosaminoglycan is bound to the bioactive glass. Exemplary glycosaminoglycans include heparin, heparan sulfate, chondroitin sulfate, dermatan sulfate, keratan sulfate, and hyaluronic acid.

Alternatively or in addition, the bioactive glass particles may include surface immobilized peptides. Peptides include any suitable peptides to complement the osteoconductivity of the bone graft. For example, peptides may include (1) bone formulation stimulators, such as B2A, P1, P2, P3, P4, P24, P15, TP508, OGP, or PTH and mixtures thereof; (2) both, bone resorption inhibitors and bone formation stimulators, such as NBD, CCGRP, or W9 (SEQ ID NO: 1) and mixtures thereof; and/or (3) bone targeting peptides, such as $(Asp)_6$ (SEQ ID NO:2), $(Asp)_8$ (SEQ ID NO:3), or (Asp, Ser, Ser)$_6$ (SEQ ID NO:4) and mixtures thereof (see e.g., App. Ser. No. 61/974,818, which is incorporated herein in its entirety). In alternative embodiments, the bioglass particles of the bone graft may be functionalized with other peptides and/or growth factors known and used in the art.

Alternatively, the porous implant may be immersed in blood, PRP, bone marrow or bone marrow concentrates to provide the signaling proteins and cells to further enhance the regeneration of the hard tissues.

Alternatively or in addition, the bioactive glass particles may further include growth factors and other therapeutic substances and drugs.

Once a specified macroporous bioactive glass scaffold is prepared, it may then be cut into various shapes and sizes and packaged into kits.

1.2 Forms

The macroporous bioactive glass scaffold materials may be processed to obtain a bone graft having a body of a suitable size and shape.

Figure 7:
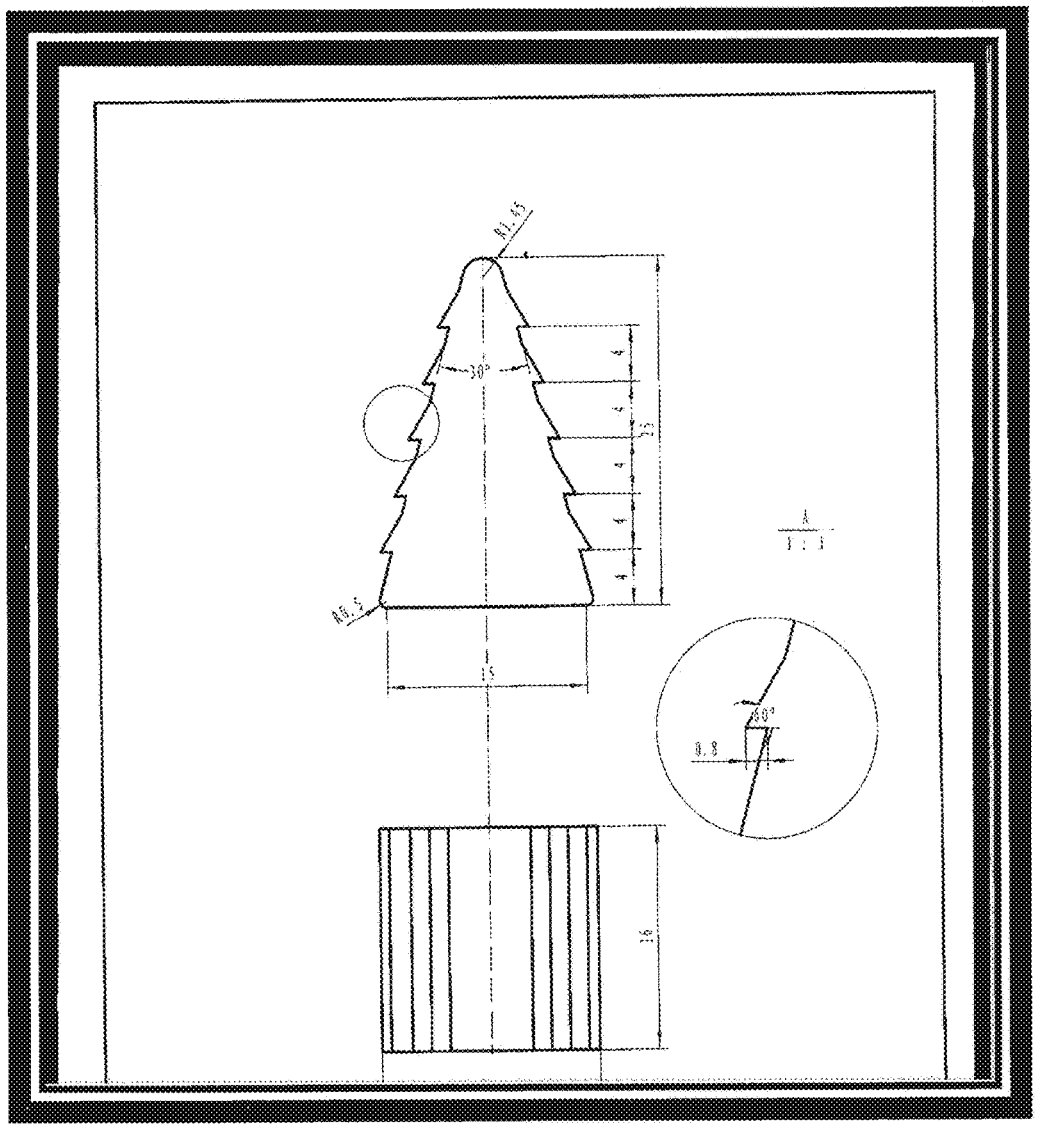
FIG. 7 depicts a drawing of an exemplary bioglass bone graft for use in children >1.5 years old.
Figure 8:
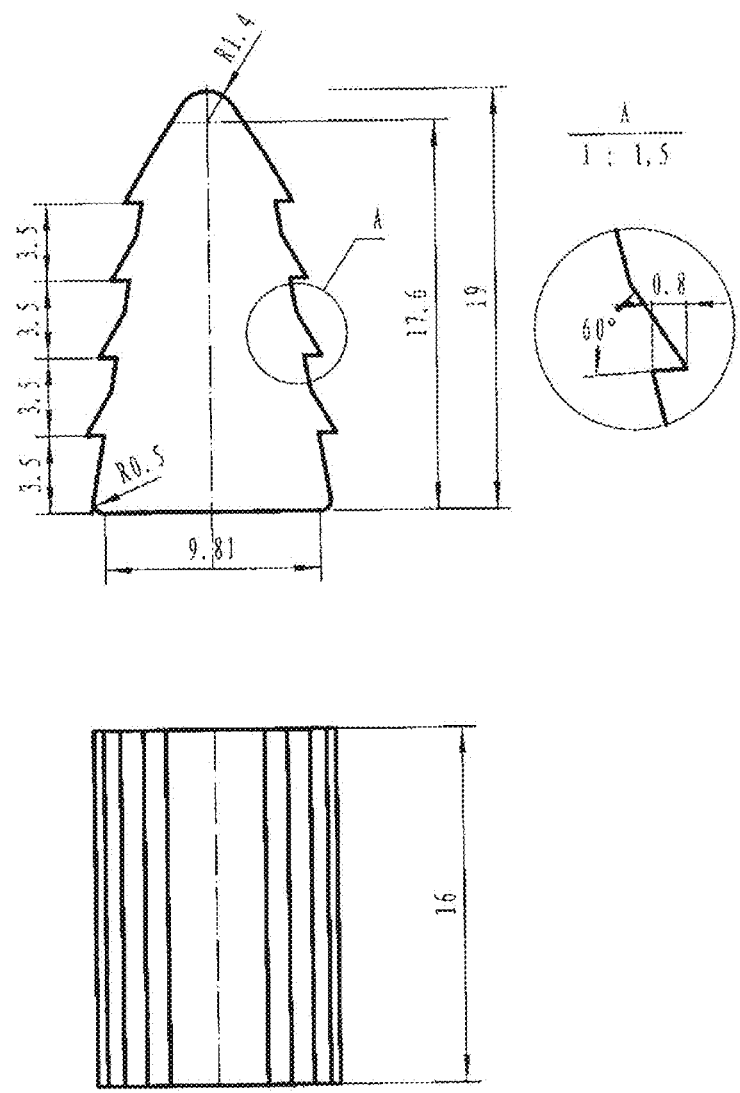
FIG. 8 depicts a drawing of an exemplary bioglass bone graft for use in children <1.5 years old.

The bone graft/implant is designed based on its clinical consideration as can be seen, for example, in FIGS. 7 and 8. Specifically, the body of a bone graft is prepared for a relatively easy placement into the defect space in a right position. Compared with iliac crest autogenous bone, the bone graft can be prepared so that the graft has different angles to meet the various requirements from clinical cases.

In some embodiments, the particles of bioglass are sintered to form porous particulate made from the bioactive glass particles. In one embodiment, fine particles of the bioactive glass are mixed with a sacrificial polymer and a binder to create a pre-shaped construct having a body of a pre-determined shape (e.g., a block, wedge, or disk). The construct is then heated under specific conditions that allow a welding of the particles together without completely melting them. As described above, this process uses a temperature high enough to allow for the polymer material to burn off leaving a porous structure. The compressive strength as well as the porosity of the construct may be controlled by varying the type and the amount of the sacrificial polymer and the sintering time and temperature used.

The bone graft can be formed into any shape as required for the specific patient and/or the surgical procedure.

Specifically, the bone graft may be prepared to form a pre-determined shape.

FIG. 7 illustrates one embodiment of the bone graft for use, e.g. in children older than 1.5 years. In the specific embodiment, the bone graft is a wedge having a length of about 25 mm, width of about 15 mm, and height of about 16 mm. The bone graft includes "teeth", where the distance between the individual teeth is about 4 mm and the length of the individual teeth is about 0.8 mm. The angle shown in FIG. 7 for individual teeth is about 60°.

FIG. 8 illustrates one embodiment of the bone graft for use, e.g., in children younger than about 1.5 years. In the specific embodiment, the bone graft is a wedge having a length of about 19 mm, width of about 9.81 mm, and height of about 16 mm. The bone graft includes "teeth", where the distance between the individual teeth is about 3.5 mm and the length of the individual teeth is about 0.8 mm. The angle shown in FIG. 7 for individual teeth is about 60°.

Clearly, depending on the desired use and the age of a patient, the sizing of the bone graft may vary. For example, the length of the bone graft may vary and be in the range of from about 5 mm to about 100 mm; the width may be in the range of from about 1.0 mm to about 75 mm; and the height may be in the range of from about 1.0 mm to about 50 mm.

As discussed above, in certain embodiments, the bone graft may be prepared with angled "teeth" on the edges, as shown in FIGS. 7 and 8 to stabilize the implant in the position without using metal pins for extra fixation. For example, the body of the bone graft comprises a top and a bottom surfaces (may be triangular, rectangular, circular, etc. in shape) and at least one side surface. At least a portion of the side surface may include a plurality of protrusions or "teeth" to facilitate prevention of expulsion of the bone graft once installed. In certain instances two or more side surfaces are present. At least a portion of the side surfaces may include a plurality of protrusions. The distance between the individual "teeth" may vary and is in the range of about 0.5 mm to about 10 mm. The angle (FIGS. 7 and 8) of the teeth may be about 60° but can also vary. The length of individual "teeth" may also vary and is in the range from about 0.5 mm to about 20 mm.

Figure 10A:
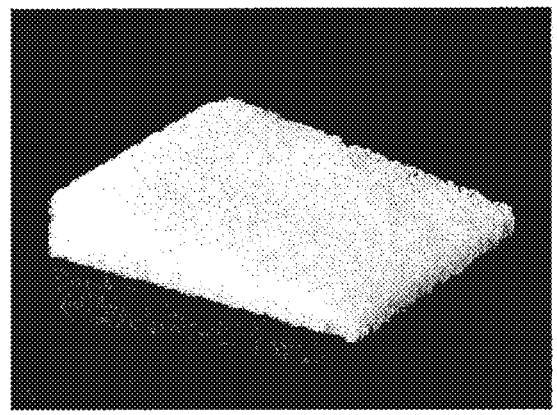
FIGS. 10A and 10B depict exemplary wedge-shaped bone grafts.
Figure 10B:
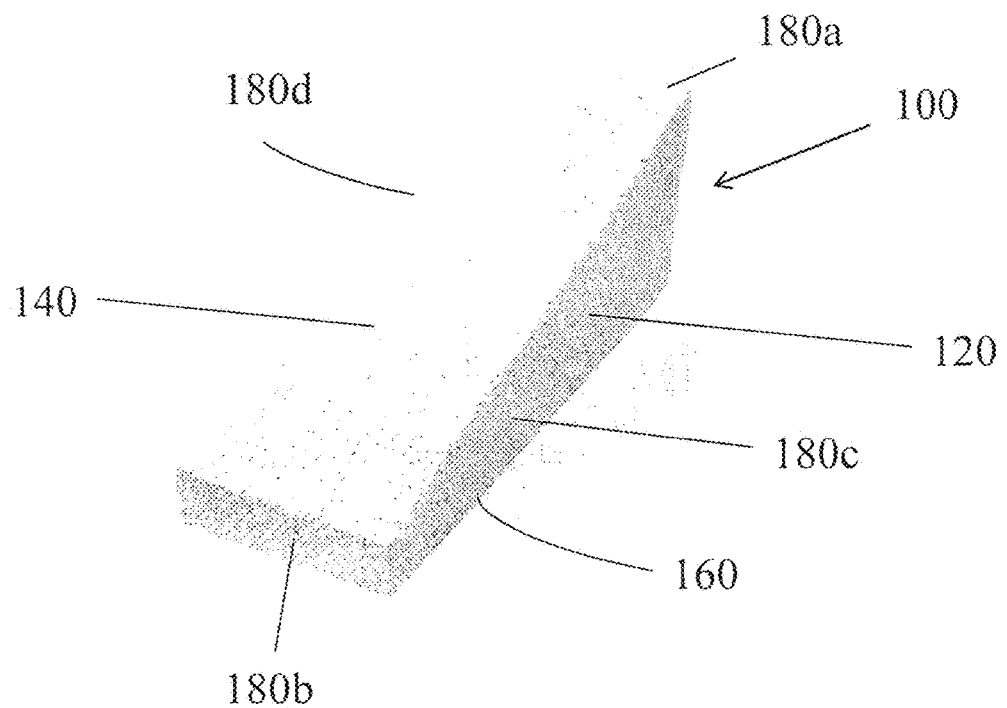

FIGS. 9A-C and FIGS. 10A-B show further exemplary shapes for of the bone grafts. For example, the bone graft may be prepared to form a block (FIGS. 9A-C) such as a cube, cuboid, cylinder or a wedge (FIGS. 10A and 10B). Other regular as well as irregular shapes may be suitable and pre-determined based on the intended use of the bone graft, such as dowel, strip, sheet, strut or disc.

The bone graft may be prepared to have a specified size.

In one exemplary embodiment, as shown in FIG. 10B, a bone graft 10 is wedge shaped and includes a body 100 that includes a top 140 and bottom 160 surfaces, wherein the top and bottom surfaces define at least one height or thickness there between and at least two sets of opposing side surfaces 18ab, 18cd, wherein the respective opposing side surfaces define a width and length of the surfaces of body, respectively.

In an exemplary embodiment, the thickness or height of the bone graft can range from approximately 0.1 mm (e.g., for sheets) to 50 mm (e.g., for blocks); alternatively, from approximately 5 mm to 25 mm; or alternatively, from approximately 5 mm to 20 mm.

The length of the bone graft may also vary and be in a range of approximately 5 mm to 100 mm.

The width may also very and be in a range of approximately 10 mm to approximately 100 mm.

In another exemplary embodiment, as shown in FIG. 9A, the bone graft may be of dowel shape, having a specified diameter. For example, a dowel may have a diameter in the range of approximately 5 mm to 50 mm, alternatively, approximately 5-10 mm; alternatively, approximately, 20-30 mm; alternatively approximately 30-40 mm; alternatively, approximately 40-50 mm.

1.3 Kits

The bone graft may be packaged into a kit. At least one, but in alternative embodiments, at least two, at least three or more bone grafts may be packaged together into a kit.

The kit may also include a tray to facilitate the addition of blood, bone marrow, glycosaminoglycans, and/or proteins, including growth factors, drugs or other bioactive molecules.

2. Preparation of Materials:

The bone graft includes a resorbable, macroporous bioactive glass scaffold characterized in that the bioactive glass scaffold has a compressive strength of at least approximately 18 MPa, porosity of approximately 40-80 volume percent, and pore size of approximately 5-600 microns, wherein the body is configured to be implanted into a prepared site in a patient's bone tissue.

The macroporous bioactive glass scaffold materials are prepared according to the methods previously described in U.S. Pat. No. 7,758,803, which is incorporated by reference in its entirety.

In certain embodiments, the higher strength compositions (compressive strength of about 17-100 MPa) are prepared through altering the composition. Specifically the amount of pore forming agents, such as PEG may be reduced to facilitate the preparation of a higher density material to have an optimized resorption time for implants capable of withstanding greater physiological loading.

The inorganic materials used in the method of preparing the bioactive glass scaffold are all of analytical purity.

In certain embodiments, the bioactive glass scaffold is prepared from bioactive glass powder prepared using the melting method. The inorganic materials applied are all of analytical purity.

Specifically, these chemical reagents are weighed and evenly mixed in line with requirements for proper composition results, and then melted in temperatures ranging from 1380° C. to 1480° C. to produce glass powders with a granularity varying from 40 to 300 μm after cooling, crushing and sieving procedures. Furthermore, such glass powders are then used as the main raw material to prepare a variety of the macroporous bioactive glass scaffold substances by way of different processing technologies.

The pore forming agents can be organic or polymer materials such as polyethylene glycol, polyvinyl alcohol, paraffin and polystyrene-divinylbenzene, etc., whose granularity can fall in the range of 50-600 microns. Thus, the pore forming agent within a certain granularity range (20-70% in mass percent) can be blended with the bioactive glass powders and the resulting mixture can be molded by adopting either of the following two approaches:

First, the dry pressing molding approach, in which 1-5% polyvinyl alcohol (concentration at 5-10%) is added to the said mixture as the adhesive, which is stirred, and then dry-pressed into a steel mold (pressure at 2-20 MPa) to produce a pellet of the macroporous material, which is then sintered (temperature at 750-900° C.) for 1-5 hours to obtain final product.

Second, the gelation-casting approach, in which an aqueous solution is prepared as per the following mass percent concentrations: 20% acrylamide, 2% N, N'-methylene-bisacrylamide cross-linking agents and 5-10% polyacrylic acid dispersant agents. Next, the aforementioned mixture and the aqueous solution (volume percent at 30-60%) is combined and mixed, and ammonium persulfate (1-5% in mass percent) and N, N,N', N'-tetramethyl ethylene diamine (1-5% in mass percent) is added. Then, the above-mentioned materials are stirred to produce a slurry with fine fluidity and homogeneity, which is then poured into plastic or plaster molds for gelation-casting. Later the cross-linking reaction of monomers is induced under temperatures ranging from 30° C. to 80° C. for 1-10 hours, and pellets of the macroporous material are obtained after a few hours of drying at 100° C. The pellets are processed first at the temperature of 400° C. to remove organics, and then sintered at 750-900° C. to obtain the macroporous material of the present invention.

3. Performance Evaluation 3.1. The Mechanical Strength of the Macroporous Material:

An array of samples obtained in this invention was tested for their respective compressive strengths using the Autograph AG-1 Shimadzu Computer-Controlled Precision Universal Tester made by the Shimadzu Corporation. The testing speed designated for these samples was 5.0 nun/min. This test revealed that the compressive strength of the macroporous material obtained according to the methods described herein can be well controlled within the scope of 1-100 MPa; alternatively within the scope of 1-16 MPa.

3.2. The Porosity of the Macroporous Materials

The Archimedes Method was used to carry out a test with a part of the samples mentioned above to determine their porosities, and a Scanning Electron Microscope (SEM) was used to observe their pore shapes and distribution. This test demonstrated that the porosity of the macroporous material obtained in this invention can be well controlled within a range of 40-80%.

3.3 Bioactivity Evaluation

A test of in vitro solution bioactivity was carried out with the macroporous materials obtained in the present invention, after being washed in de-ionized water and acetone successively, and then air dried afterwards. The solution applied was simulated body fluids (SBF). The ion and ionic group concentrations in this SBF are the same as those in human plasma. This SBF's composition is as below:

| | |
|---|---|
| NaCl: | 7.996 g/L |
| $NaHCO_3$: | 0.350 g/L |
| KCl: | 0.224 g/L |
| $K_2HPO_4 \cdot 3H_2O$: | 0.228 g/L |
| $MgCl_2 \cdot 6H_2O$: | 0.305 g/L |
| HCl: | 1.000 mol/L |
| $CaCl_2$: | 0.278 g/L |
| $Na_2SO_4$: | 0.071 g/L |
| $NH_2C(CH_2OH)_3$: | 6.057 g/L |

The test was carried out with macroporous material immersed in SBF in the following conditions: 0.15 g of macroporous material, 30.0 ml/day SBF, 37° C. in a temperature-controlled water-bath. After the macroporous material was immersed in SBF for a period of 1, 3 or 7 days respectively, samples were taken out and washed using ion water, and then underwent the SEM, Fourier Transform Infrared spectrometry (FTIR) and XRD tests. The respective results of the tests can be seen in FIGS. 3, 4A-C and 5. The relevant bioactivity experiment results have shown that the macroporous glass scaffold materials obtained in the present invention can induce the formation of bone-like hydroxyapatite on their surface, indicating ideal bioactivity of these materials.

3.4 Degradability Evaluation

A bioactivity experimental test was conducted on the macroporous materials in this invention after being washed in de-ionized water and acetone successively, and then dried. Evaluation of both degradation speed and degradability of the macroporous materials according to the content of $SiO_2$ substances that are released at different time points after the materials have been immersed in SBF was conducted. For example, where PEG is used as the pore forming agent, the macroporous bioactive glass scaffolds (porosity at 40%) obtained after the processes of dry pressing molding and calcination (temperature at 850° C.) exhibit a degradability of 10-20% when the scaffold has been immersed in SBF for 5 days.

4. Methods

In certain embodiments the bone grafts/implants may be used in orthopedic, spine, trauma and dental applications, and specifically in methods of correcting a deformity in a bone (e.g., congenital or one resulting from trauma). As such certain embodiments relate to methods of using the bone grafts for regeneration of hard tissues, especially for joint reconstruction (i.e. developmental dysplasia of the hip or DDH, and tibial plateau elevation), craniomaxillofacial reconstruction and spine fusion are provided.

In certain other embodiments, the bone graft may be for use as a replacement or support for living bone materials in surgical procedures requiring the use of bone graft material.

In certain embodiments, the methods may include preparing a site in a patient's bone tissue (e.g., by resecting the bone to create a resection) and inserting into the open site in the patient's bone tissue at least one individual bone graft comprising a body formed to define a predetermined configuration and including a resorbable, macroporous bioactive glass scaffold comprising in mass percent approximately 15-45% CaO, 30-70% $SiO_2$, 0-25% $Na_2O$, 0-17% $P_2O_5$, 0-10% MgO and 0-5% $CaF_2$ and characterized in that the bioactive glass scaffold has a compressive strength of at least approximately 17 MPa, porosity of approximately 40-80 volume percent, and pore size of approximately 5-600 microns, wherein the body is configured to be implanted into a prepared site in a patient's bone tissue.

In certain embodiments, tools may be necessary to prepare a site in a patient including for preparing resection. Such tools are known to those skilled in the art. For example, in certain embodiments, opening the resection to a height at which the deformity is corrected may be accomplished using an opening tool. Exemplary methods of opening a resection, such as during an osteotomy procedure, were previously described in U.S. Pat. No. 6,823,871, which is incorporated herein in its entirety.

Certain embodiments relate to the use of the bone graft for regeneration of hard tissues, such as joints, as a result of a congenital defect or trauma.

Specifically, certain embodiments relate to methods of treating or correcting DDH in a subject.

Figure 6A:
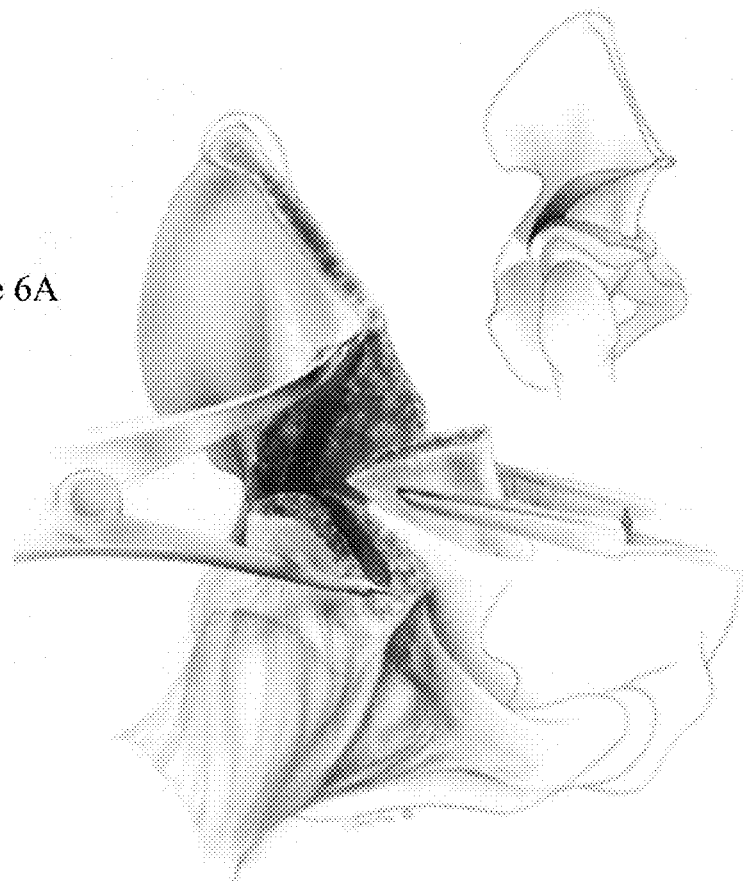
FIG. 6A depicts a drawing of an iliac crest adapted to reconstruct the undeveloped hip cup.
Figure 6B:
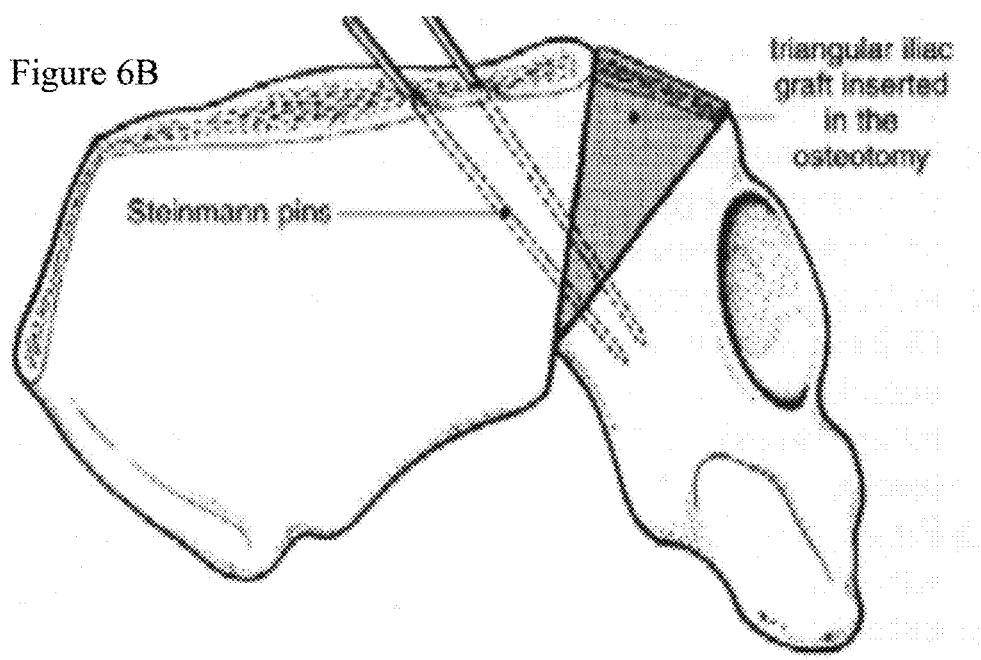
FIG. 6B depicts a drawing of an iliac crest with an irregular iliac graft inserted in the osteotomy site.

DDH is a common defect, which affects infants and young children. In general, the hip is a "ball-and-socket" joint. In a normal hip, the femoral head (ball) at the proximal end of the thighbone (femur) fits firmly into the acetabulum (socket), which is a part of the pelvis. In infants and children with DDH, the hip joint has not formed normally. The femoral head is loose within the socket and may be easy to dislocate. Dislocation may occur as a result of the poor development of the acetabular cup which does not effectively cover the femoral head. This defect leads to biomechanical instability resulting in a malfunction of the hip. Early treatment, i.e., before the age of 1 is highly recommended for infants with DDH. Several treatment options are available at that stage. However, if the abnormality is identified late and cannot be resolved with conservative treatment, surgery must be conducted to reconstruct the acetabulum of the hip joint. The surgery involves reconstruction and positioning of the cup and femur head connection to facilitate normal functioning and subsequent growth of the patient's hip. The most common surgical procedure involves cutting the bone of the pelvis above the acetabulum followed by correcting the angle of the acetabulum and placement of a bone graft to fill the space created from repositioning the cup as shown in FIGS. 6A-B.

Currently, autogenous bone from the iliac crest is adapted clinically to fill the space. However, children, generally, have small and thin iliac crest, which is insufficient in quantity to fill the space. In addition, the iliac crest may not be strong enough to support the pressed cup so that the space angle could be reduced after surgery, resulting in some degree of the dislocation and leading to potential failure of the surgery.

The method of correcting or treating DDH in a subject includes providing to the subject the bone graft composition described herein. The method may also include resecting the bone and packing the resection with at least one bone graft into the open resection. As opening tool may be used, if necessary.

In certain embodiments relating to the methods of treating or correcting developments dysplasia of the hip using osteotomy methods and bone graft compositions described herein. The term "osteotomy," in practice, refers to reshaping a bone. When the pelvic side of the socket is repaired, it is called "pelvic osteotomy." There are several different types of pelvic osteotomy and the choice depends on the shape of the socket and the surgeon's experience. When the upper end of the thigh bone is re-shaped, this is called "femoral osteotomy." Each of these procedures may be done alone, in combination, or together with a reduction. Children older than 2 years almost always need all three procedures to make the hip stable and return it to a more normal shape. An arthrogram (x-ray dye injected into the hip joint) at the beginning of the surgery can help the surgeon decide exactly what needs to be corrected. Whether one or all three procedures are performed, the recovery time is about the same. The child is usually in the hospital for 2 or 3 nights and in a body cast for 6-8 weeks. That is generally followed by bracing full-time or part-time for another 6-12 weeks. For some osteotomy procedures, pins and plates are used. They are removed after the bone is healed. That may range from eight weeks for the pelvis to one year for the femur. Typically, they can be removed after a few months, but up to three years after surgery. The bone graft compositions may be placed into the osteotomy site.

Certain other embodiment relate to methods of changing the shape of the hip joint using osteotomy methods and bone graft compositions described herein. Surgery to change the shape of the hip joint typically involve re-shaping the shallow hip socket (acetabulum) so it is in a better position to cover the ball of the hip joint (femoral head). Osteotomies may be performed on the hip socket side of the joint or on the ball side of the joint (upper thigh bone). As noted above, surgeries are on the hip socket side are called "acetabular osteotomies" or "pelvic osteotomies." The periacetabular osteotomy (PAO) is the most common type for young adults also called the Ganz or Bernese osteotomy. When the top of the thigh bone is re-shaped (just below the hip joint on the ball side of the joint) these surgeries are called "femoral osteotomies" and may be "varus osteotomies," or "valgus osteotomies" depending on the specific procedure being performed. Surgery to restore the shape of the joint is currently more common on the hip socket side with a procedure, called a PAO. The bone graft compositions may be placed into the osteotomy site.

Osteotomy methods as well as resecting methods are known in the art.

In certain other embodiments, the bone graft/implants that are wedge-shaped blocks may be used as osteotomy wedges in the treatment of tibial plateau compression fractures and other bone anomalies requiring the insertion of a bone graft to alter the angle of an articulating joint or change in the axis of a bone, which was compromised through a congenital defect or trauma. The bone graft comprises a body formed to define a predetermined configuration and including a resorbable, macroporous bioactive glass scaffold comprising in mass percent approximately 15-45% CaO, 30-70% $SiO_2$, 0-25% $Na_2O$, 0-17% $P_2O_5$, 0-10% MgO and 0-5% $CaF_2$ and characterized in that the bioactive glass scaffold has a compressive strength of at least approximately 17 MPa, porosity of approximately 40-80 volume percent, and pore size of approximately 5-600 microns.

A tibial plateau often follows a fracture or crushing injury to one or both of the tibial condyles resulting in a depression in the articular surface of the condyle. In conjunction with the compression fracture, there may be a splitting fracture of the tibial plateau. Appropriate treatment for compression fractures depends on the severity of the fracture. Minimally displaced compression fractures may be stabilized in a cast or brace without surgical intervention. However, more severely displaced compression with or without displacement fractures are treated via open reduction and internal fixation.

Typically, the underside of the compression fracture is accessed either through a window cut (a relatively small resection) into the side of the tibia or by opening or displacing a splitting fracture. A bone elevator may then be used to reduce the fracture and align the articular surface of the tibial condyle. A fluoroscope or arthroscope may be used to visualize and confirm the reduction. A bone graft may then be placed into the cavity under the reduced compression fracture to maintain the reduction. If a window is cut into the side of the tibia, the window may be packed with graft material and may be secured with a bone plate. If a splitting fracture was opened to gain access, then the fracture is reduced and may be stabilized with bone screws, bone plate and screws, or a buttress plate and screws.

In certain other embodiments, the bone graft/implants may be used in craniomaxillofacial reconstruction. Craniomaxillofacial reconstruction is the surgical intervention to repair cranial defects. The aim of craniomaxillofacial reconstruction is not only a cosmetic issue; also, the repair of cranial defects gives relief to psychological drawbacks and increases the social performances. The method includes preparing a site for craniomaxillofacial reconstruction and inserting into the prepared site the bone graft composition comprising a body formed to define a predetermined configuration and including a resorbable, macroporous bioactive glass scaffold comprising in mass percent approximately 15-45% CaO, 30-70% $SiO_2$, 0-25% $Na_2O$, 0-17% $P_2O_5$, 0-10% MgO and 0-5% $CaF_2$ and characterized in that the bioactive glass scaffold has a compressive strength of at least approximately 17 MPa, porosity of approximately 40-80 volume percent, and pore size of approximately 5-600 microns.

In certain other embodiments, the high strength, porous, bioactive osteostimulative, bioglass scaffolds may be shaped for use as an intervertebral spacer to promote spine fusion in the treatment of degenerative disc disease and trauma. The bioglass scaffold comprises a body formed to define a predetermined configuration and including a resorbable, macroporous bioactive glass scaffold comprising in mass percent approximately 15-45% CaO, 30-70% $SiO_2$, 0-25% $Na_2O$, 0-17% $P_2O_5$, 0-10% MgO and 0-5% $CaF_2$ and characterized in that the bioactive glass scaffold has a compressive strength of at least approximately 17 MPa, porosity of approximately 40-80 volume percent, and pore size of approximately 5-600 microns.

In certain other embodiments, at least two individual bone grafts may be inserted within a prepared site in a patient (e.g., resection); alternatively, three or more individual bone grafts are inserted within the site.

EXAMPLES

Implementation Example 1

The raw materials used in this example are the same as those described above.

Figure 2:
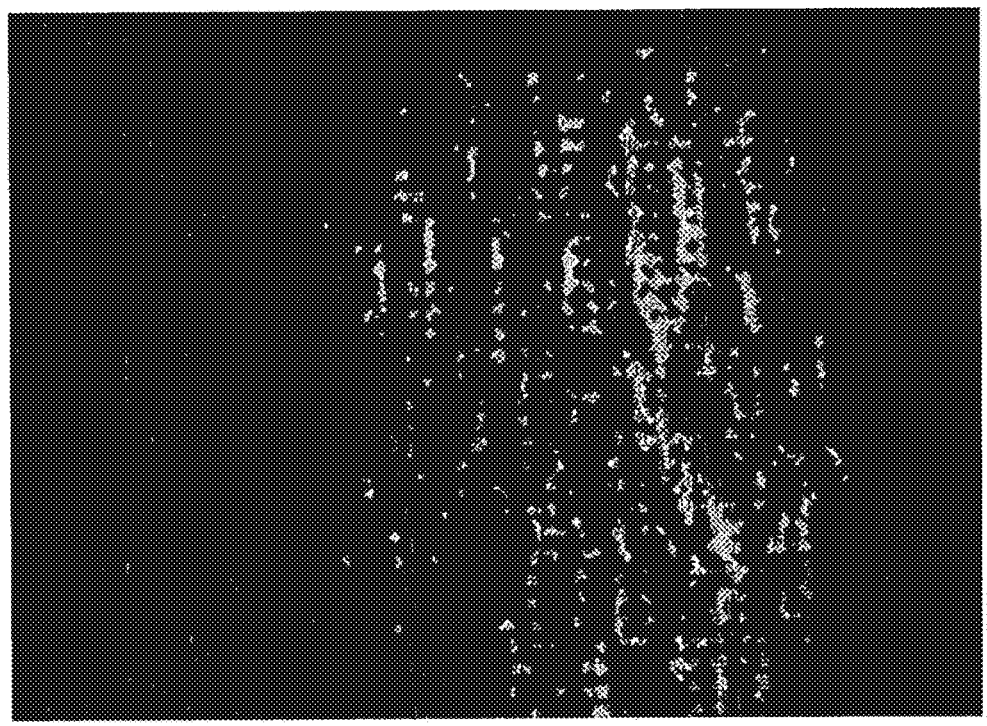
FIG. 2 is an optical microscope picture displaying cross-sections of the macroporous bioactive glass.

$SiO_2$, $Na_2CO_3$, $CaCO_3$ and $P_2O_5$ (all of analytical purity) are mixed proportionally, and the mixture is melted into homogenous fused masses at the temperature of 1420° C. and then cooled, crushed and sieved to obtain bioactive glass powder with a particle diameter ranging from 40-300 microns. The composition of the bioactive glass powder is expressed as CaO 24.5%, $SiO_2$ 45%, $Na_2O$ 24.5% and $P_2O_5$ 6%. Next, the bioactive glass powder (150-200 microns in granularity) is mixed with the polyethylene glycol powder (200-300 microns in granularity) at a mass percent of 60:40. Polyvinyl alcohol solution (6%), which serves as the adhesive, is added and the solution is mixed. The mixture is then dry-pressed under a pressure of 14 MPa, and the pellets of the macroporous materials are stripped from the mold. The pellets are first processed at 400° C. to remove organics, and then sintered at 850° C. for 2 hours to obtain the said macroporous materials with a compressive strength at approx. 1.25 MPa and a porosity at about 56%. The XRD indicates the existence of both the $Ca_4P_2O_9$ and $CaSiO_3$, as shown in FIG. 2.

Finally, the said macroporous materials are immersed in simulated body fluids (SBF) for periods of 6 hours and 1, 3, and 7 days respectively, and evaluated as to both bioactivity and resorbability/degradability. Results in FIGS. 4A-C and 5 demonstrate that the macroporous glass material of this invention has strong bioactivity, as a bone-like apatite layer is soon formed on the surface of such materials after they are immersed in SBF. After this material has been immersed in SBF for 5 days, its degradation rate can be up to a level of 14%, suggesting that the macroporous bioactive glass material in this invention has ideal degradability, and can therefore be expected to be successfully applied for the restoration of injured hard tissues and as the cell scaffold for in vitro culture of bone tissue.

Implementation Example 2

$SiO_2$, $CaCO_3$, $Ca_3(PO4)_2$, $MgCO_3$, $CaF_2$ (all of analytical purity) are mixed proportionally, melted into a homogenous fused masses at the temperature of 1450° C., and then cooled, crushed and sieved to obtain bioactive glass powder (particle diameter ranging from 40-300 microns). The composition of the bioactive glass powder is CaO 40.5%, $SiO_2$ 39.2%, MgO 4.5%, $P_2O_5$ 15.5% and $CaF_2$ 0.3%.

Next, the bioactive glass powder is blended with polyvinyl alcohol powder (300-600 microns in granularity) at a mass percent of 50:50 to obtain a solid mixture. An aqueous solution composed of 20% acrylamide, 2% N,N'-Methylene-bis-acrylamide and 8% polyacrylic acid is prepared, and 10 grams of the said solid mixture is blended with the aqueous solution at a volume percent (ratio) of 50:50, with several drops of ammonium persulfates (3% in mass percent) and several drops of N,N,N',N'-tetramethyl ethylene diamine (3% in mass percent) added and stirred to produce a slurry with fine fluidity, which is poured into molds for gelation-casting. The cross-linking reaction of monomers of the material is induced for 3 hours at 60° C. In this way, pellets of the macroporous material are obtained by stripping them from the mold after the gelation-casts have been dried at 100° C. for 12 hours. Subsequently, the pellets are processed at 400° C. to remove organics, and then sintered at 850° C. for 2 hours to produce the macroporous materials that feature a compressive strength at about 6.1 MPa and porosity at approx. 55%. This material demonstrated degradability is 78% (calculated based on the mass percent of Si releasing) after being immersed in Simulated Body Fluids for 3 days.

Implementation Example 3

The raw materials and the preparation methods of the bioactive glass powder used in this example are the same as those in Implementation Example 2.

The bioactive glass powder (granularity at 150-200 microns) is blended with PEG powder (granularity at 200-300 microns) at the mass ratio of 40:60. Polyvinyl alcohol solution (concentration at 6%) is added to serve as the adhesive and mixed. This mixture is dry-pressed under a pressure of 14 MPa, and pellets of the macroporous materials are obtained by removal from the mold. The pellets are first processed at 400° C. to remove organics, and then sintered at 800° C. to obtain the said macroporous materials with a compressive strength at approx. 1.5 MPa and porosity at about 65%. After being immersed in Simulated Body Fluids for 3 days, the degradation rate of the macroporous glass material is 38% (calculated based on the mass percent of Si releasing).

Implementation Example 4: Wedge for Tibial Plateau Elevator and DDH Blocks $SiO_2$, $Na_2CO_3$, $CaCO_3$ and $P_2O_5$ (all of analytical purity) were mixed proportionally, and the mixture was melted into homogenous fused masses at the temperature of 1420° C. and then cooled, crushed and sieved to obtain bioactive glass powder with a particle diameter ranging from 100-300 microns.

The composition of the bioactive glass powder was expressed as CaO 24.5%, $SiO_2$ 45%, $Na_2O$ 24.5% and $P_2O_5$ 6%.

Figure 3:
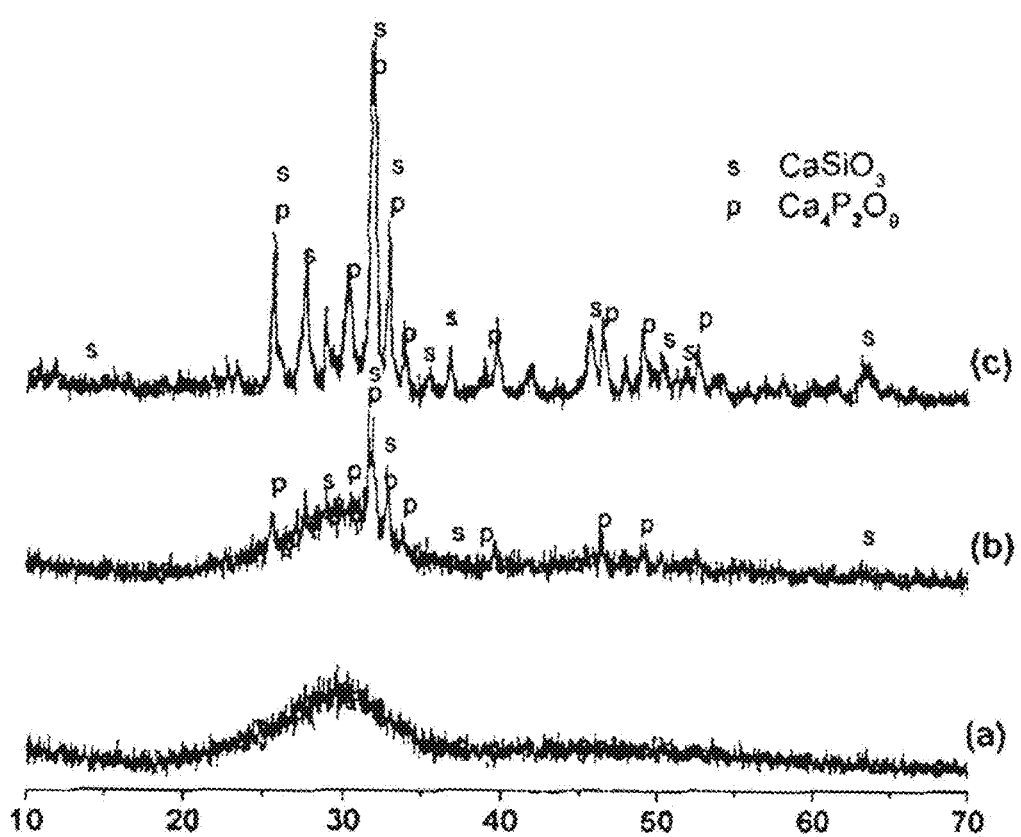
FIG. 3 shows XRD displays for the macroporous bioactive glass materials prepared under different temperatures; these illustrations show that different levels of crystallization of calcium silicate or calcium phosphate can be found on the surface of the materials prepared under different temperatures; (a) bioactive glass powder before sintering, (b) bioactive glass scaffolds prepared by sintering at 800° C., (c) bioactive glass scaffolds prepared by sintering at 850° C.
Figure 4A:
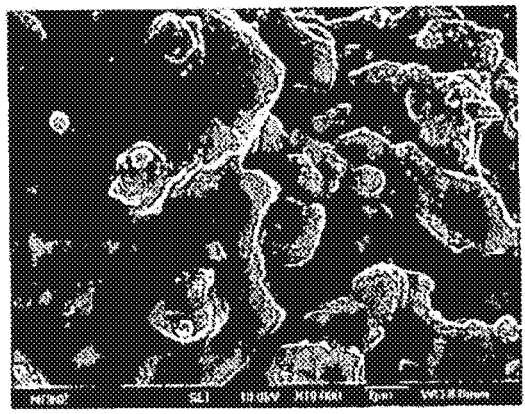
FIG. 4A is an SEM picture of the macroporous bioactive glass material of this invention before being immersed in SBF (i.e. simulated body fluids)
Figure 4B:
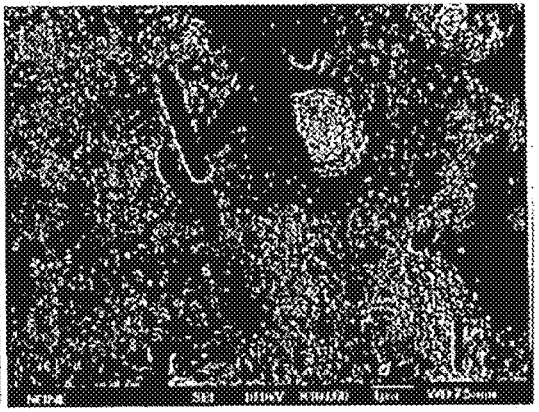
FIG. 4B is an SEM picture of the material immersed SBF for 1 day.
Figure 4C:
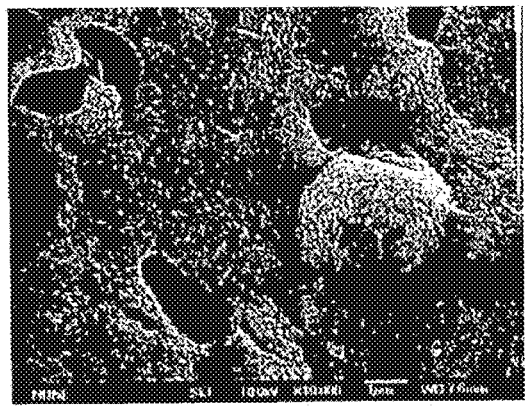
FIG. 4C is an SEM picture of the material when immersed in SBF for over 3 days; these pictures show that substantial hydroxyapatite crystalline can form on the surface of the material when immersed in SBF for 1 day.
Figure 5:
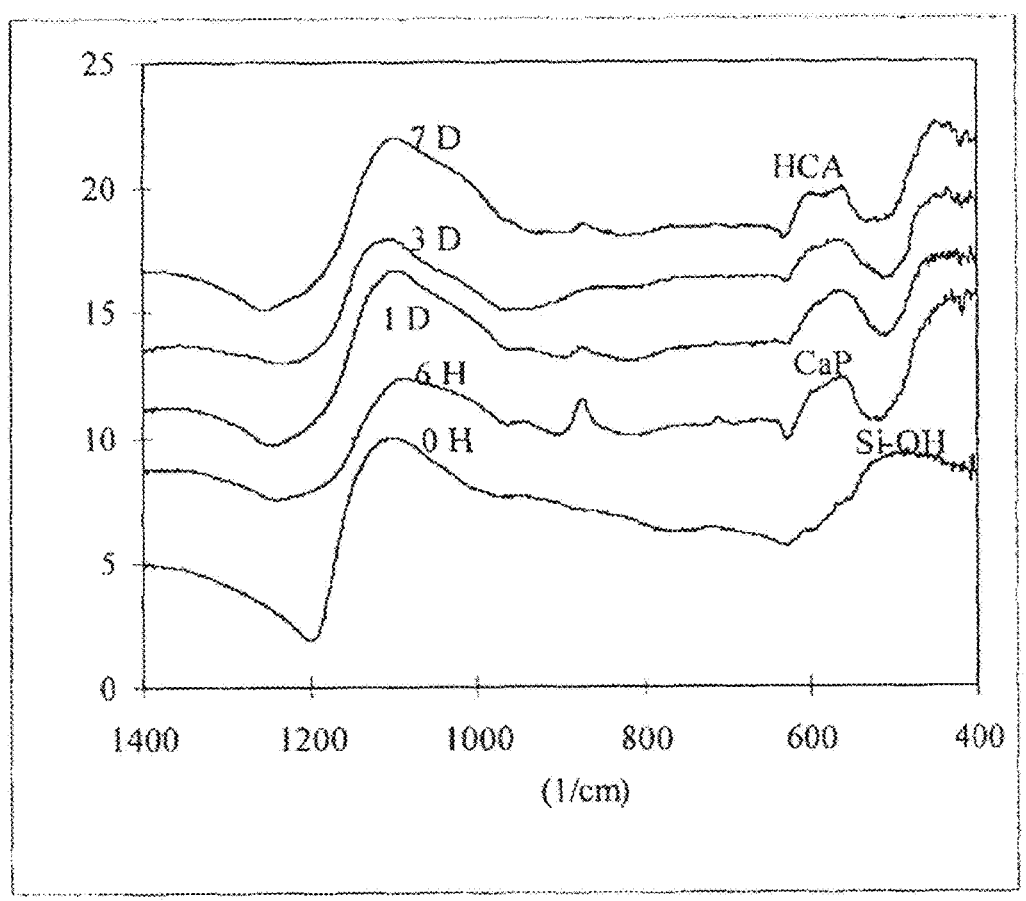
FIG. 5 is a Fourier Transform Infrared spectrometry (FTIR) spectra of the macroporous bioactive glass materials before being immersed in SBF, as well as after being immersed in SBF for 0 hours, 6 hours, 1 day, 3 days and 7 days respectively; the resulting analysis reveals that the hydroxyl-apatite peak can be observed when such material has been immersed in SBF for only 6 hours.

Next, the bioactive glass powder (100-300 microns in granularity) was mixed with the polyethylene glycol powder (400-600 microns in granularity) at a mass percent of 70:30. Polyvinyl alcohol solution (6%), which serves as the adhesive, was added and the solution was mixed. The mixture was then dry-pressed under a pressure of 14 MPa, and the green bodies of the macroporous materials were stripped from the mold. The green bodies were first processed at 400° C. to remove organics, and then sintered at 900° C. for 6 hours to obtain the macroporous materials with a compressive strength at approx. 16 MPa and a porosity at about 40%. The XRD indicated the existence of both the $Ca_4P_2O_9$ and $CaSiO_3$, as shown in FIG. 3.

Figure 12A:
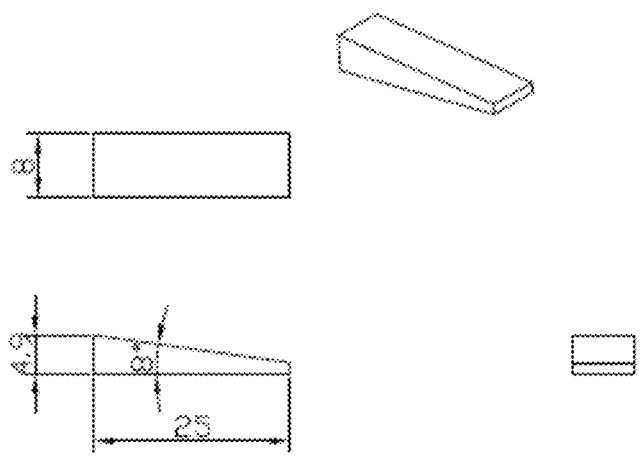
FIGS. 12A, 12B and 12C show exemplary wedge design graphs with angles 8°, 10°, 12°, respectively.
Figure 12B:
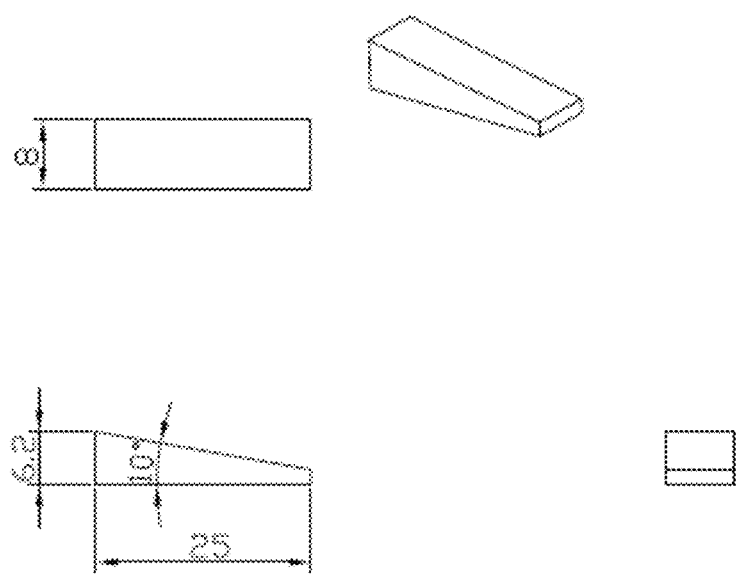
Figure 12C:
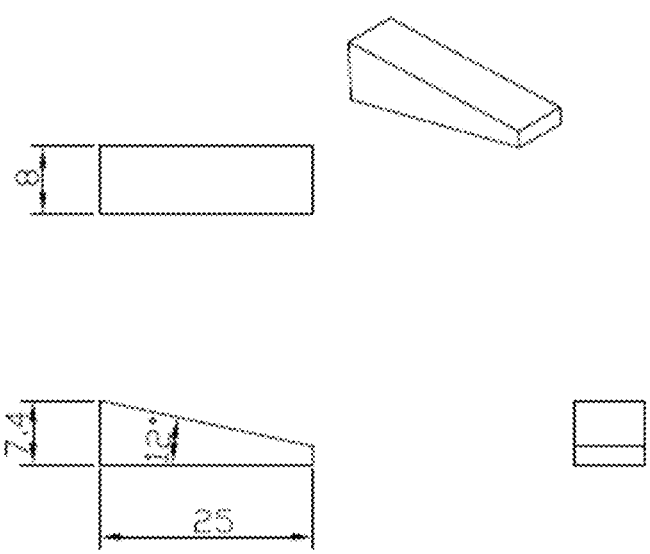

FIGS. 12A, 12B and 12C show exemplary wedge design graphs with angles 8°, 10°, 12°, respectively.

It is understood and contemplated that equivalents and substitutions for certain elements and steps set forth above may be obvious to those skilled in the art, and therefore the true scope and definition of the invention is to be as set forth in the following claims.

The invention claimed is:

1. A resorbable, macroporous bioactive glass scaffold comprising in mass percents approximately 15-45% CaO, 30-70% $SiO_2$, 0-25% $Na_2O$, 0-17% $P_2O_5$, 0-10% MgO and 0-5% $CaF_2$, wherein the bioactive glass scaffold has a porosity of between approximately 50 to 80 volume percent, the pores ranging in size from approximately 50 to 600 microns, and are interconnected, and wherein the compressive strength of the scaffold is between approximately 16 to 100 MPa.

2. The bioactive glass scaffold of claim 1, comprising approximately 24.5% CaO, 45% $SiO_2$, 24.5% $Na_2O$ and 6% $P_2O_5$ and having a porosity of approximately 56 volume percent.

3. The bioactive glass scaffold of claim 1, comprising approximately 40.5% CaO, 39.2% $SiO_2$, 4.5% MgO, 15.5% $P_2O$, and 0.3% $CaF_2$ and having a porosity of approximately 55 volume percent.

4. The bioactive glass scaffold of claim 1, further comprising at least one of precipitated calcium phosphate or calcium silicate crystals.

5. The bioactive glass scaffold of claim 1, wherein the bioactive glass scaffold comprises a side surface, wherein at least a portion of the side surface comprises a plurality of protrusions to facilitate prevention of expulsion or dislocation of the bioactive glass scaffold once installed in a patient.

6. The bioactive glass scaffold of claim 1, wherein the bioactive glass scaffold is in a predetermined configuration selected from the group consisting of a block, a wedge, a dowel, a strip, a sheet, a strut, a disc.

7. The bioactive glass scaffold of claim 1, wherein the bioactive glass scaffold further comprises a glycosaminoglycan selected from the group consisting of heparin, heparan sulfate, chondroitin sulfate, dermatan sulfate, keratan sulfate, and hyaluronic acid.

8. The bioactive glass scaffold of claim 1, wherein the bioactive glass scaffold further comprises one or more of surface-immobilized peptides, growth factors and therapeutic agents.

9. The bioactive glass scaffold of claim 8, wherein the peptides are selected from the group consisting of WP9QY (W9; SEQ ID NO:1), OP3-4, RANKL, B2A, P1, P2, P3, P4, P24, P15, TP508, OGP, PTH, NBD, CCGRP, $(Asp)_6$ (SEQ ID NO:2), $(Asp)_8$ (SEQ ID NO:3), and $(Asp, Ser, Ser)_6$ (SEQ ID NO:4), and mixtures thereof.

10. The bioactive glass scaffold of claim 1, wherein the bioactive glass scaffold is pre-treated with blood, PRP, bone marrow or a bone marrow concentrate to provide signaling proteins and cells to further enhance the regeneration of the hard tissues.

11. The bioactive glass scaffold of claim 1, wherein the scaffold can be used as material for the restoration of injured hard tissues in a subject.

12. The bioactive glass scaffold of claim 1, wherein the scaffold can be used as the cells support scaffold for in vitro culture of bone tissue.

13. The bioactive glass scaffold of claim 1, wherein the bioactive glass scaffold is for use as a replacement or support for living bone materials in surgical procedures requiring the use of bioactive glass scaffold.

14. The bioactive glass scaffold of claim 1, wherein the bioactive glass scaffold is for use in a joint reconstruction procedure, tibial plateau elevation procedure, craniomaxillofacial reconstruction, spine fusion procedure, or treating or correcting developmental dysplasia of the hip in a subject.

15. A method of treating or correcting developmental dysplasia of the hip in a subject comprising
  resecting the bone to create a resection; and
  placing the bioactive glass scaffold of claim 1 in the resection such that the bioactive glass scaffold spans the resection.

* * * * *